United States Patent [19]
Little

[11] 4,271,846
[45] Jun. 9, 1981

[54] LEAD INSTALLATION TOOL
[75] Inventor: Richard L. Little, Minneapolis, Minn.
[73] Assignee: Daig Corporation, Minnetoka, Minn.
[21] Appl. No.: 32,661
[22] Filed: Apr. 23, 1979
[51] Int. Cl.³ .............................................. A61N 1/04
[52] U.S. Cl. .................................................. 128/785
[58] Field of Search ............................... 128/784–786, 128/410 P, 642

[56] References Cited
U.S. PATENT DOCUMENTS

| 3,737,579 | 6/1973 | Bolduc ................................. 128/785 |
| 3,875,947 | 4/1975 | Jula et al. ............................. 128/785 |
| 3,943,936 | 3/1976 | Rasor et al. ....................... 128/419 P |

FOREIGN PATENT DOCUMENTS

| 2823307 | 12/1978 | Fed. Rep. of Germany ........... 128/642 |
| 2247263 | 5/1975 | France .................................... 128/785 |
| 387716 | 9/1973 | U.S.S.R. ................................. 128/786 |

OTHER PUBLICATIONS

Mechanical Engineering, p. 48, Jan. 1967.

Primary Examiner—Lee S. Cohen
Attorney, Agent, or Firm—Clayton R. Johnson

[57] ABSTRACT

A tool for installing a body implantable electrode of a lead that includes an electrode holder assembly having a clamp for releasably clamping an electrode mounting head and a clamp operator conductor carrier assembly rotatably mounted by the holder assembly for operating the clamp from a head clamping position to a head release position. The carrier assembly has a chamber and a bore for holding part of the lead conductor.

39 Claims, 9 Drawing Figures

LEAD INSTALLATION TOOL

BACKGROUND OF THE INVENTION

A lead installation tool for holding a lead while the electrode thereof is being screwed into body tissue.

In U.S. Pat. No. 3,737,579 there is disclosed a device for screwing an electrode into body tissue, the device having a chamber for holding the electrode mounting head, and a radially outwardly opening groove to have the lead conductor forced thereinto. Apparently the head forms a friction fit with the device. In this type of device a rod is used to push the electrode head out of the friction fit. This requires careful manipulation to prevent undesired movement of the electrode once it is screwed into the heart tissue.

In another prior art device a rod and outer sleeve assembly is attached to the lead by means of pins in the rod end. After lead placement in the heart tissue, the desirable method of removal is to support the sleeve and pull back on the rod (move it axially) thereby stripping the lead off the pins. Whether the rod is pulled back, or the sleeve is pushed forward, is difficult to determine. Hence the same undesirable movements is generated.

To provide a tool that overcomes problems such as the above, this invention has been made.

SUMMARY OF THE INVENTION

A lead installation tool that includes an electrode holder assembly having a clamp operable between an electrode head portion clamping position and a release position, and a clamp operator rotatably mounted by the holder assembly to operate the clamp between a clamp position and a release position.

One of the objects of this invention is to provide a lead installation tool having a new and novel clamp means for releasably holding a lead electrode mounting head. Another object of this invention is to provide a body tissue lead installation tool having new and novel means for resiliently holding an electrode mounting head and releasing the head without applying any significant force to the head.

A further object of this invention is to provide new and novel means for clampingly holding an electrode mounting head and utilizing relative rotary movement for releasing the clamping engagement with the head. A still further object of this invention is to provide a new and novel rotary cam operated clamp for releasably holding the electrode mounting head of a lead for conducting electrical impulses to body tissue.

Figure 1:
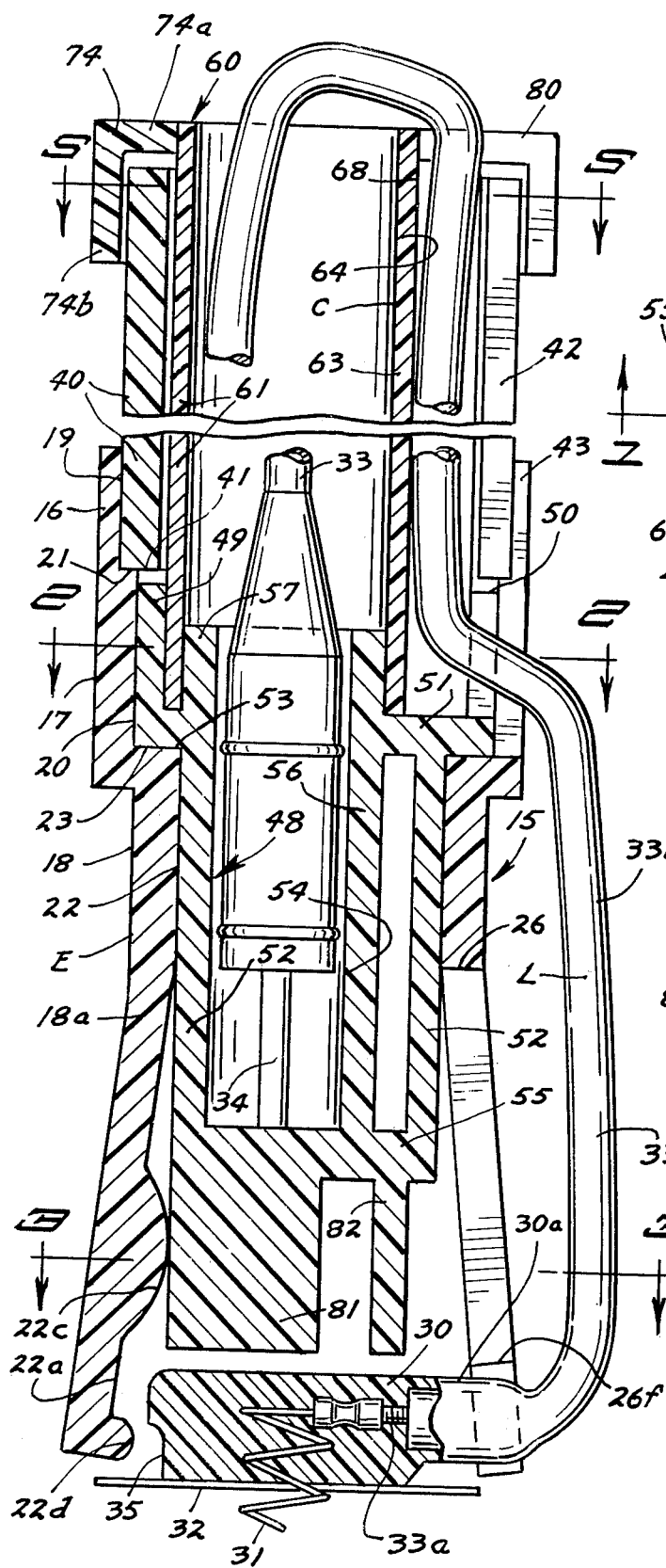
FIG. 1 is a longitudinal cross sectional view of the lead installation tool of the first embodiment of the invention in an unclamped position with an axial intermediate position being broken away and a lead with the electrode end portion thereof being shown in cross section, said view being generally taken along the line and in the direction of the arrows 1—1 of FIG. 2.

Referring in particular to FIG. 1, the lead installation tool of this invention includes a clamp operator conductor carrier assembly C mounted for limited rotational movement by an electrode holder assembly E for releasably clamping the distal end portion of a conventional lead L that is used for conducting electrical pulses to body tissue, for example, that of a heart. The lead L includes an electrically nonconductive, generally cylindrical head 30 that mounts an electrically rigid helical electrode 31 which has a number of helices, including at least one that extends outwardly of the head and through the circular piece of netting 32 that is mounted by the head. One end of an elongated electrically conductive portion 33a, which may be either coiled or noncoiled metal wire, of an elongated conductor 33 is electrically connected to the end portion of the electrode that is located within the head while the opposite end thereof is electrically connected to the connector pin 34. The conductor includes an electrical insulation layer 33b surrounding portion 33a from the head to the connector pin.

The electrode holder assembly E includes a tubular clamp, generally designated 15, having an axial outer tubular end portion 16 that at its axial inner end is joined to the outer end of the tubular axially intermediate portion 17, and an axially inner reduced outer diameter tubular portion 18 that at its axial outer end is integrally joined to the axial inner portion of intermediate portion 17. Portion 16 has a central bore 19 that opens to central bore 20 of portion 17 which is of a smaller diameter than bore 19 to provide an axially outwardly facing annular shoulder 21. The reduced diameter portion 18 has a central bore 22 that opens to bore 20 and is of a smaller diameter than bore 20 to provide an axially outwardly facing annular shoulder 23.

The reduced diameter portion 18 is provided with a plurality of axially elongated equally circumferentially spaced slots 26 that open through the axial inner terminal end thereof and that are located a substantial distance from the axial outer end thereof to provide a plurality of axially elongated clamp segments 18a (for example 3). The inner peripheral wall of each segment includes a circular wall portion 22a and a rounded protrusion 22c that extends radially inwardly of the wall portion 22a, the protrusions being located axially intermediate the opposite ends of the cam segments and equally circumferentially spaced from the axial segment slot edges 26a that in part define the respective segment. To the axial inner end of one of the clamp segments there is integrally joined an abutment portion 22d that is arcuately elongated and extends a substantial distance radially inwardly of wall portion 22a. The abutment portion is of a size and shape to fit within the downwardly and radially outwardly opening notch 35 of the lead head, the notch being diametrically opposite the radially outward extension 30a of the head through which the conductor 33 extends The segment slot 26 that is diametrically opposite abutment portion 22d has an enlarged downwardly notched portion 26f that is of a size and shape to have head portion 30a extend radially therethrough even when the clamp segments are in their clamp position. The clamp is made of a plastic material that resiliently maintain the clamp segments to have an inner diameter at their inner ends that is the same as that of portion 18 axially remote from the segments, except at the protrusions and abutment 22d.

An axially elongated clamp mounting tube 40 extends into clamp bore 19 to abut against shoulder 21 and is fixedly joined to the tubular clamp. The mounting tube is of a smaller inner diameter than the diameter of bore 20 whereby there is provided an axially inwardly facing, generally annular shoulder 41 that extends radially inwardly of clamp portion 17. Further, the mounting tube has a slot 42 extending axially therethrough, slot 42 being axially aligned with a slot 43 that extends axially through clamp portion 16 and a major part of the axial length of portion 17. Clamp portion 17 has a circumferentially elongated slot 44 that opens to slot 43 and to shoulder 23, the circumferential dimension of slot 44 being at least twice the circumferential dimension of each of slots 42, 43. The axial height of slot 44 may be about the same as the circumferential dimension of slot 42. Slot 42 is axially aligned with notch 26f.

The clamp operator conductor carrier assembly C includes a cam member, generally designated 48, that includes an axially outer tubular portion 49 of an axial length that is slightly less than the axial spacing of shoulders 23, 41, of an outer diameter to form a close rotatable fit with the inner peripheral wall of clamp portion 17, and of an inner diameter slightly less than the inner diameter of mounting tube 40. Due to shoulders 41, 23 extending radially more closely adjacent the tool central axis X than the outer periphery of portions 49, 51, the clamp operator assembly C is prevented from moving any significant amount axially relative the electrode holder assembly E. Tubular portion 49 has a slot 50 extending axially therethrough that is of about the same circumferential dimension as that of slot 42. A disk portion 51 is integrally joined to the axial inner end of portion 49, a reduced diameter tubular portion 52 having its axial outer end joined to the disk portion to provide a downward facing annular shoulder 53 that is seatable on shoulder 23. Portion 52 is of an outer diameter to form a close rotatable fit with the inner peripheral wall of clamp portion 18 axially outwardly of slots 26. The axial inner end of tubular portion 52 is integrally jointed to disk portion 55.

A circumferentially curved wall portion 56 has circumferentially spaced axial edges integrally joined to the inner peripheral wall of reduced diameter portion 52 along the axial length thereof to in conjunction therewith define a circular bore 54 that opens to disk portion 55. An annular portion 57 is integrally joined to disk portion 51 and portions 52, 56 to have bore 54 extend axially therethrough, i.e. the bore extending through disk portion 51. The central axis of reduced diameter portion 52 is coextensive with the central axis X of electrode holder assembly while the central axis of Y of bore 54 is located intermediate axis X and the inner peripheral wall of the part of portion 52 that defines part of bore 54, and is angularly spaced from slot 50. Thus on the diametric opposite side of axis X from axis Y circumferential portion 56 is substantially radially spaced from clamp portion 52, and the radial spacing of annular portion 57 from portion 49 is substantially greater than it is on the same side of axis Y from axis X. Portion 57 does not extend axially outwardly of disk portion 51 as far as portion 49.

An axially elongated operator conductor carrier, generally designated 60, includes a tubular portion 61, which is of a radial thickness that is about as the minimum radial spacing of cam portions 49, 57, extends between said portions into abutting relationship with disk portion 51 and is fixedly joined to cam 48. The tubular portion 61 has a central axis coextensive with axis X and a radially outwardly opening slot 62 extending the axial length thereof that is axially aligned with slot 50 and opens radially outwardly through the adjacent part thereof, the circumferential dimensions of slots 50, 62 being about the same. The slot 62 opens radially through tubular portion 61. Tubular portion 61 extends axially outwardly a greater distance from shoulder 23 than portion 40.

A circumferential curved wall portion 63 has circumferentially spaced axial edges integrally joined to the inner peripheral wall of tubular portion 61 along the axial length thereof to in conjunction therewith define a circular bore 64 that has a central axis coextensive with axis Y. Annular portion 57 extends in abutting relationship with the axial inner part of the inner peripheral wall portions that define bore 64. Chamber wall portions 66, 67 are integrally joined to portions 61, 63 along the length thereof to provide a chamber 68 that opens to slot 62, the chamber in one transverse direction being about the same as the circumferential dimension of each of slots 50, 62. The chamber is elongated in a circumferential direction to extend angular away from slot 62 in the opposite angular direction that slot 44 extends away from slot 43.

An annular knob 74 has an annular radial flange 74a fixedly joined to the axial outer end portion of tubular portion 61 and an axial flange 74b joined flange 74a to extend in part concentrally with reference to tubular portion 40 and be located radially outwardly thereof. The knob has a slot 80 extending through its flanges to open to slot 62 and is of about the same circumferential dimension as slot 42.

Figure 2:
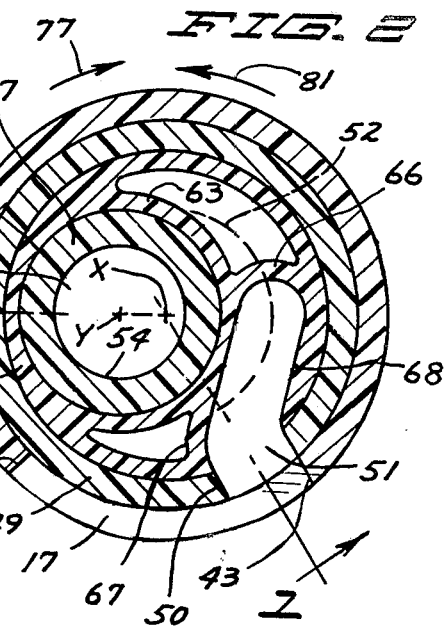
FIG. 2 is a transverse cross sectional view of the installation tool that is generally taken along the line and in the direction of the arrows 2—2 of FIG. 1.
Figure 3:
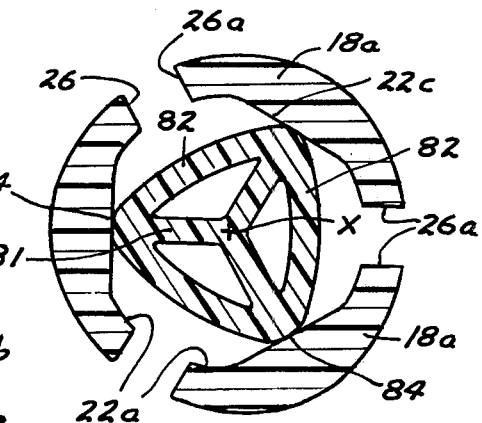
FIG. 3 is a transverse cross sectional view generally taken along the line and in the direction of the arrows 3—3 of FIG. 1 to show the clamp and clamp operating cam.
Figure 5:
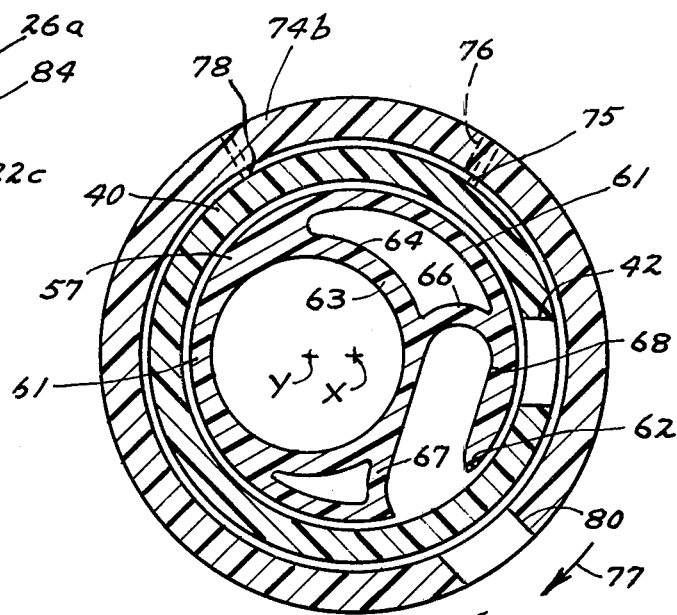
FIG. 5 is a transverse cross sectional view generally taken along the line and in the direction of the arrows 5—5 of FIG. 1 other than the illustrated structure is a clamped position.
Figure 6:
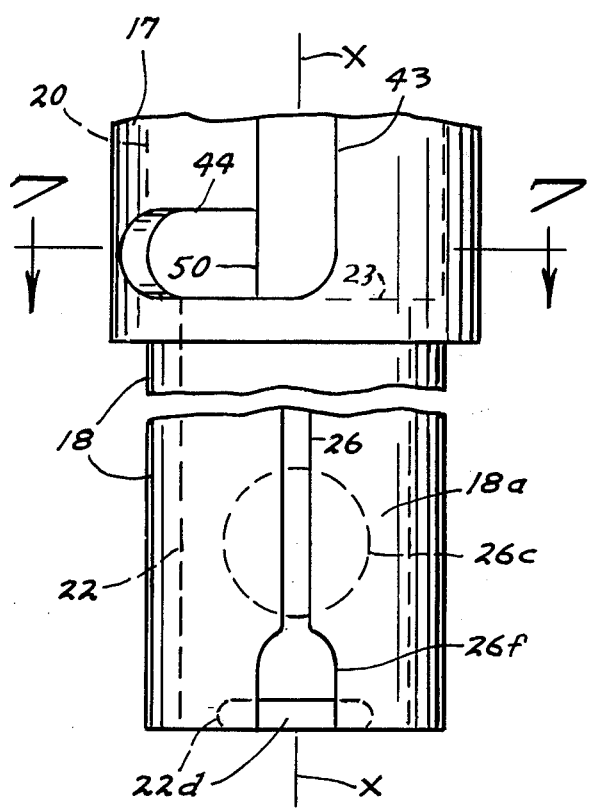
FIG. 6 is a fragmentary longitudinal view of the clamp of the first embodiment, other than only one of the clamp protrusions and cam segment slots is shown, an axially intermediate portion being broken away.
Figure 7:
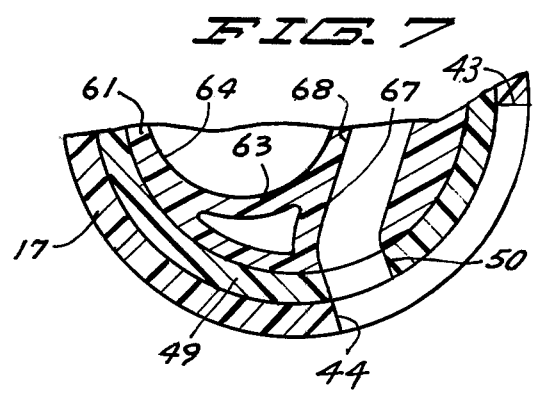
FIG. 7 is a fragmentary transverse cross sectional view of the structure shown in FIG. 2 other than the conductor carrier and clamp mounting tube are shown in a clamped position.

Axially adjacent knob flange 74b, a stop 75 is fixedly joined to tubular portion 40 to extend radially outwardly thereof while a second stop 78 is fixedly joined to the tubular portion 40 to extend radially outwardly thereof. The second stop 78 is angularly spaced from stop 75. A knob protrusion 76 is fixedly joined to knob flange 74b to be located angularly between stops 75, 78 and to be abuttable against one of the stops, depending on the direction of rotation of the clamp operator assembly relative the holder assembly E. When the clamp operator assembly is rotated in the direction of arrow 81 relative the holder assembly, the rotation thereof is limited by protrusion 76 abutting against stop 78. When the protrusion abuts against stop 78, the installation tool is in its lead head release position of FIG. 2. When the clamp operator assembly is rotated in the direction of arrow 77 relative the holder assembly to the position of FIG. 5, protrusion 76 abuts against stop 75 and the tool is in its lead head clamping position.

Figure 4:
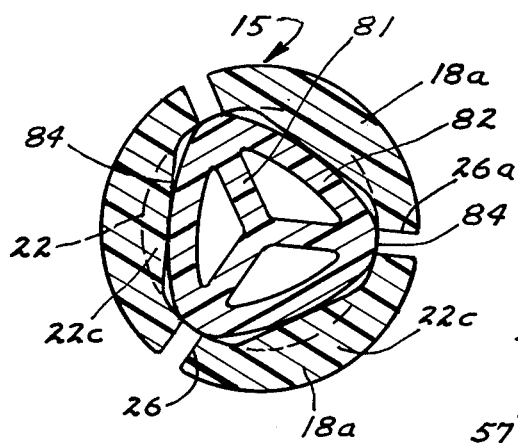
FIG. 4 is a view the same as FIG. 3 other than the clamp and clamp operating cam are shown in a clamped position.

The cam 48 has its disk portion 55 located axially outwardly of clamp protrusions 22c. The cam includes a cam member 81, 82 joined to disk portion 55 to extend axially inwardly thereof and includes a plurality of radially extending spokes 81 that are integrally joined at their one ends and have opposite ends equally circumferentially spaced from one another. Extending between each adjacent pair of spokes and integrally joined to said opposite ends thereof are arcuate sections 82 to provide equally angular spaced cam surfaces 84 that are equal radially spaced from the central axis X. The radial spacing of the cam surfaces 84 from axis X is substantially greater than the minimum radial spacing of the protrusions 22c from said axis X when the clamp is in the clamp position of FIG. 4 and is less than the radius of bore portion 22a. Further, as may be noted in FIG. 4, in the clamp position, cam surfaces 84 are angularly adjacent slots 26, and the part of the outer peripheral wall of sections 82 that are of minimum radial spacing from axis X are radially adjacent the part of protrusions 22c that are most closely adjacent said axis.

In using the apparatus of this invention to implant the electrode 31 in body tissue, the clamp operator assembly is in a position that knob protrusion 76 abuts against stop 78, the relative positions of the tool assemblies being shown in FIGS. 1-3 and 6. At this time cam surfaces 84 are angularly about midway between slots 26 and in abutting relationship to the radial thickest part of the cam protrusions 22c whereby the axial inner ends of the cam segments are located a substantially greater distance from axis X than the dimension of the radius of bore 18 axially outwardly of slots 26. Further, at this time slots 42, 62 are radially aligned. With the axial inner end of the clamp axially adjacent the lead head 30 and notch 26f adjacent head portion 30a, the conductor 33 is threaded through slots 43, 50 to extend into the lower end of chamber 68, then axially outwardly through the chamber, and thence reversely bent to extend into bore 64 whereby the connector pin 34 is located in either bore 64 or bore 54, depending on the length of the lead. With the head extending into bore 22, knob 74 is rotated in the direction of arrow 77 until the knob protrusion abuts against stop 75. As the knob is thus rotated the cam surfaces 84 move into engagement with cam protrusion surface portions that are of progressively further radial spacing from axis X and thence off said surfaces to be radially aligned with slots 26. This results in the axial inner ends of the cam segments resiliently moving more closely adjacent the axis X with cam protrusion 22d moving into notch 35 and the remaining parts of the segments inner ends moving into abutting relationship with the circumferential cylindrical wall part of the head. The head extension extends through notch 26f whereby the clamp cannot rotate any significant amount relative the lead head. Further since the axially inner transverse surface of the cam member 81,82 is axially closely adjacent the surface of the head that is axially opposite netting 32 and protrusion 22d in extending into notch 35 abuts against a head surface opposite the surface that is adjacent the cam, the head is prevented from moving any significant amount axially relative the holder assembly. Thus the head is clampingly engaged.

As the knob is rotated in the direction of arrows 77 relative the holder assembly, slots 43, 62 are moved angularly out of radial alignment with slot 42, this movement being permitted by slot 44. Thus the part of the conductor that extends through chamber 68 is locked therein to extend through slot 44 remote from slot 43. This twists the part of the conductor between slot 44 and head extension 30a and takes up some of the slack in this part of the conductor.

With the head clamped the electrode 31 extends axially inwardly thereof. The tool is moved to move the electrode into contact with the body tissue and the entire tool rotated in the direction of the arrow 77 to screw the electrode into the body tissue. After the electrode is implanted, knob 74 is rotated in the direction of arrow 81 until the knob protrusion abuts against stop 78. This moves the cam surfaces into abutting relationship with cam protrusions 22c. This moves the axial inner ends of the cam segments radially away from the axis X to their head release position. Further, the slots 43, 50, 42 are now radially aligned with slots 62, 80, and the conductor pin end portion is moved out of bore 64, and the conductor is moved out of chamber 68 and through slots 42, 62. Thence the tool is withdrawn to leave the electrode in an implanted position.

Since the holder assembly is not rotated to moved axially to release the head, nor any part of the tool moved axially relative one another to release the head, no force is exerted on the head as the tool is operated from its clamping position to its release position.

Figure 8:
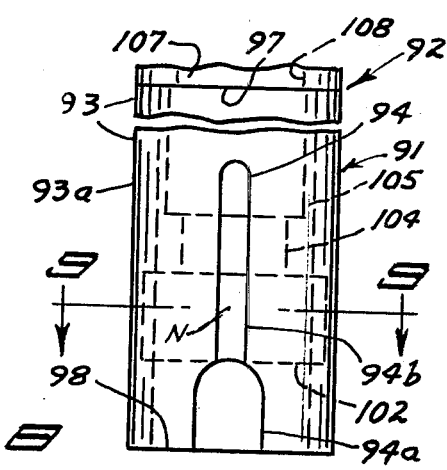
FIG. 8 is a fragmentary longitudinal view of the second embodiment with an axial intermediate portion broken away, said view being generally taken along the line and in the direction of arrows 8—8 of FIG. 9.
Figure 9:
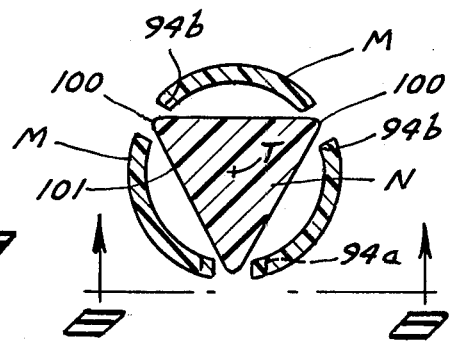
FIG. 9 is a transverse cross sectional view generally taken along the line and in the direction of arrows 9—9 of FIG. 8, said view showing the cam in an unclamped position.

Referring to FIGS. 8 and 9, the second embodiment of the invention includes an electrode holder assembly, generally designated 91, which mounts a clamp operator assembly, generally designated 92, for limited rotational movement relative thereto. The electrode holder assembly 91 comprises an axially elongated tubular member 93 that may be of constant inner and outer diameters throughout its length, the distal (axial inner) end portion 93a thereof constituting a tubular clamp that is mounted by the remainder of the tubular member. Portion 93a is provided with a plurality of axially elongated, equally circumferentially spaced slots 94 that open through the axial inner terminal thereof and that are located a substantial distance from the axial terminal end 97 of tubular member 93 to provide a plurality of axially elongated clamp segments M (for example 3). Each segment is a constant inner diameter throughout its length. One segment slot has an enlarged downwardly opening notched portion 94a that is of size and shape to have an electrode head portion 30a extend radially therethrough, even when the clamp segments are in their clamp position. Tubular member 93 is made of a plastic material that resiliently maintains the clamp segments M to have an inner diameter at their inner terminal ends 98 that is the same as the diameter of the tubular member axially remote from the slots.

The clamp operator 92 includes a cam member N that in transverse cross is of a generally equalateral triangular shape, provided there are three slots 94. The apexes (cam surfaces) 100 of cam member are rounded, the maximum spacing thereof from the central axis T of tubular member 93 being greater than the radius of curvature of the inner peripheral walls of the cam segments M, but less than the radius of curvature of the outer peripheral wall thereof. Thus, when the cam member is in an unclamped position neither the apexes nor the side walls 101 thereof abut against the clamp segments, the apexes extending into the slots.

The axial inner transverse surface 102 of the cam member during use is located axially outwardly of terminal end 98 about the same distance as the juncture of the slot portion 94b to notch 94a is located from terminal end 98. The opposite transverse surface is integrally joined to a cylindrical portion 104. Cylindrical portion 104 in turn is integrally joined to one end of an axially elongated tube 105. Tube 105 is of a smaller diameter than the inner diameter of tubular member 93, but that is larger than the diameter of cylindrical portion 104. The tube extends within the tubular member 93.

An annular knob 107 has a central axial bore 108 of a smaller diameter than tube 105 and has its inner end joined to tube 105. The outer diameter of knob 107 may be the same as the outer diameter of tubular member 93. Knob 107 in abutting against tubular edge 97 limits the movement of cam member N toward edge 98 while apexes 100 may abut against the ends of slots 94 remote from edge 98 to limit the movement of the rod in the opposite axial direction. The cam member is thus prevented from moving axially to exert a pushing force on an electrode head clamped by segments M.

Tubular member 93 has axially elongated slotted portions (not shown) that are axially aligned with notch 94b, located axially between edge 97 and the end of tube 105 that is joined to cylindrical portion 104, open to the tube, and are of a circumferential width to form a friction fit with lengths of conductor 33b.

The tubular member 93 and the tube have cooperating means, for example a circumferential slot (not shown) in the tubular member and a protrusion (not shown) on the tube that extends into the circumferential slot to limit the rotation of the tube in the tubular member 93 between an electrode head release position and an electrode head clamping position shown in FIG. 9. In the release position, the cam member apexes abut against the inner peripheral walls of the cam segments circumferentially about midway between slot portions 94b. Since the distance from tubular member 93 and tube 105 central axis T to apexes 100 is greater than the radius of curvature of the inner peripheral walls of the cam segments, as the apexes move out of slot positions 94b into abutting relationship with the cam segments, the inner terminal end portions thereof are moved radially outwardly. Since the clamp segments M do not have a protrusion such as 22d of the first embodiment of FIGS. 1–7, the electrode head does not have to be provided with a notch 35. The slotted portion 94a functions the same as notch 26f.

In use the cam member N is operated from a release position to a clamp position so that the clamp segments hold the electrode head, conductor portions are pressed into the slotted portions of the buular member and the connector pin end of the lead extended into bore 108. After the electrode is screwed into body tissue the cam is operated to a release position, conductor portions peeled out of the slotted portions, and the installation tool withdrawn.

What is claimed is:

1. A body tissue lead installation tool for clampingly holding the head of a lead for conducting electrical impulses to body tissue, comprising an electrode holder assembly having means operable between a clamping position for clampingly engaging an electrode head and a position to release the clamped head, the clamping means having a central axis, and means mounted by the clamping means in a substantially fixed axial position on the clamping means for rotation about said axis for operating the clamping means between its positions.

2. The tool of claim 1 further characterized in that the clamping means includes a cam operated clamp operable between a clamping position and a release position, and tubular means for mounting the clamp, and that the means for operating the clamping means includes a rotatable cam for operating the clamp between its release position and its clamping position.

3. The tool of claim 2 further characterized in that the clamp extends axially away from the tubular means and has a plurality of circumferentially spaced, axially elongated slots to define a plurality of clamp segments.

4. The tool of claim 3 further characterized in that the clamp is made of a resilient material whereby the clamp segments are resiliently retained in a clamping position.

5. A body tissue lead installation tool for clampingly holding the head of a lead that has an elongated conductor for conducting electrical impulses to body tissue, comprising an electrode holder assembly having clamp means operable between a clamping position for clampingly engaging an electrode head and a position to release the clamped head, the clamp means including a cam operated clamp operable between a clamping position and a release position, and tubular means for mounting the clamp, the clamp extending axially away from the tubular means, having a plurality of circumferentially spaced, axially elongated slots defining a plurality of clamp segments and being made of a resilient material whereby the clamp segments are resiliently retained in a clamping position, and means rotatably mounted by the clamp means for operating the clamp means between its positions, the means for operating the clamp means including a rotatable cam for operating the clamp between its release position and its clamping position and an axially elongated member rotatably extended in the tubular means in a fixed axial position relative thereto and joined to the cam for rotating the cam.

6. The tool of claim 5, further characterized in that the clamp has wall portions defining an axially elongated bore opening axially opposite the tubular means and has a central axis, said slots opening to said bore, said wall portions defining a protrusion for each segment that extends radially inwardly toward the clamp axis, and are circumferential spaced from the circumferentially adjacent slots, and that the cam has a cam surface for each protrusion that in a clamp release position is of a greater radially spacing from the clamp axis than the minimum radially spacing of the protrusions from the clamp axis and is located between a pair of circumferentially adjacent protrusions.

7. The tool of claim 6 further characterized in that one of the slots has an enlarged notched portion opening axially away from the tubular means, and that one of the clamp segments is diametrically opposite said notched portion and has an abutment member extending radially toward the central axis and is axially remote from the tubular means.

8. The tool of claim 5 further characterized in that the elongated member has a first terminal end remote from the cam, wall portions defining an axially elongated chamber, and a radially outwardly opening slot that opens to the chamber, the slot opening through the first terminal end, and that the tubular means has a terminal end remote from the clamp and an axially elongated slot opening through the tubular means terminal end, the tubular means slot opening radially to the elongated member slot when the clamp is in a release position.

9. The tool of claim 8 further characterized in that the elongated member extends through the tubular means, the tubular means having a circumferentially elongated slot opening to the first mentioned tubular means slot, the circumferential slot being axially remote from the tubular means terminal end and opening radially to the elongated member slot when the clamp is in a clamped position, the first mentioned tubular means slot being angularly offset from the elongated member slot when the clamp is in a clamping position.

10. The tool of claim 8 further characterized in that the tubular means has a central axis, that the elongated member has wall means defining an axially extending bore that is spaced from said chamber, opens through the elongated member terminal end and has a central axis radially offset from the tubular means central axis.

11. The tool of claim 8 further characterized in that the elongated member and tubular means have cooperating means for limiting the rotation of the elongated member relative the tubular means between a clamp release position and a clamp clamping position.

12. A body tissue lead installation tool for clampingly holding the head of a lead for conducting electrical impulses to body tissue, comprising an electrode holder assembly having a central axis and a clamp, said clamp having a first portion that has a first end, a plurality of circumstantially spaced clamp segments joined to said first portion first end for movement between a lead head clamping position and a lead head release position, and axially elongated first means for mounting said first portion, and second means mounted in a substantially fixed axial position on the first means for movement relative thereto for moving the clamp segments between a lead head clamp position and a release position.

13. The tool of claim 12 further characterized in that the first means has means for mounting the second means for rotary movement.

14. A body tissue lead installation tool for clampingly holding the head of a lead that has an elongated conductor for conducting electrical impulses to body tissue, comprising an electrode holder assembly having a central axis and a clamp, said clamp having a first portion that has a first end, a plurality of circumferentially spaced clamp segments joined to said first portion first end for movement between a lead head clamping position and a lead head release position, and first means for mounting said first portion, and second means mounted on the first means for movement relative thereto for moving the clamp segments between a lead head clamp position and a release position, each of the first and second means having terminal ends and means defining axially elongated slots opening through the terminal ends and that in the second means clamp release position open radially to one another and radially outwardly of said axis and in the second means clamped position are angularly offset for lockingly containing at least part of the length of the conductor.

15. The tool of claim 14 further characterized in that the second means has wall portions defining an axially elongated bore opening through its terminal end that is spaced from the second means slot.

16. The tool of claim 14 further characterized in that the first means has a circumferentially elongated slot located intermediate the clamp and the first means terminal end, and opening to the first means axially elongated slot, the second means slot being of a circumferential dimension that is substantially smaller than the circumferential dimension of the first means circumferential slot.

17. A body tissue lead installation tool for clampingly holding the head of a lead for conducting electrical impulses to body tissue, comprising an electrode holder assembly having a central axis and a clamp, said clamp having a first portion that has a first end, a plurality of circumferentially spaced clamp segments joined to said first portion first end for movement between a lead head clamping position and a lead head release position, and first means for mounting said first portion, and second means mounted on the first means for movement relative thereto for moving the clamp segments between a lead head clamp position and a release position, the first means being tubular and having means for mounting the second means for rotary movement, and the second means extending within the tubular means.

18. The tool of claim 17 further characterized in that the second means has an enlarged diametric portion and that the clamp and first means having axially spaced annular shoulders adjacent and on axially opposite sides of the enlarged diametric portion that each is of an inner diameter that is less than the outer diameter of the enlarged diametric portion.

19. The tool of claim 17 further characterized in that there is provided knob means joined to the second means for rotating the second means relative the first means and cooperating means on the first means and one of the second means and the knob means for limiting the rotational movement of the second means relative the first means.

20. A body tissue lead installation tool for clampingly holding the head of a lead that has an elongated conductor for conducting electrical impulses to body tissue, comprising an electrode holder assembly having a central axis and a clamp, said clamp having a first portion that has a first end, a plurality of circumferentially spaced clamp segments joined to said first portion first end for movement between a lead head clamping position and a lead head release position, and first means for mounting said first portion, and second means mounted on the first means for movement relative thereto for moving the clamp segments between a lead head clamping position and a release position, the clamp segments defining a bore portion, and the second means including cam means located in the clamp segments bore portion for moving the clamp segments from their clamped position to their release position.

21. The tool of claim 20 further characterized in that clamp segments each have wall portions defining an inner peripheral circular bore surface portion and a wall portion defining a protrusion that in a clamp segment clamping position extend more closely adjacent said axis than said circular bore surface portions, said cam means having cam surfaces that are moved to force the protrusions away from said axis as the second means is moved from its clamped position to its release position.

22. The tool of claim 21 further characterized in that the clamp is made of a resilient material that in a relaxed condition resiliently retains the clamp segments in a clamping position.

23. The tool of claim 21 wherein the lead head is generally cylindrical, has an extension extending radially outwardly and a notch generally diametrically opposite the extension, further characterized in that there are at least three clamp segments, that an adjacent pair of segments define an outwardly opening notch for receiving the head extension and that a segment diametrically opposite the clamp notch has an abutment extending radially inwardly toward said axis for movement into the head notch.

24. The tool of claim 21 further characterized in that the second means includes means rotatably mounted by the first means for mounting the cam means and rotating the cam means about said axis to move the clamp segments from their clamping position to their release position.

25. The tool of claim 24 further characterized in that the means for mounting the cam means comprises an axially elongated member having wall portions defining an axially elongated radially outwardly opening chamber for receiving a part of the conductor and an axially elongated bore for receiving another part of the conductor, and that the first means has wall portions for defining a slot to have the above mentioned part moved therethrough and into the chamber when the second means is in a clamping position, the elongated member being rotatably extended through the first means.

26. For implanting in body tissue a body tissue electrode mounted by a lead head and electrically connected to an elongated conductor, an installation tool comprising first means defining an axially elongated, radially outwardly opening chamber for having at least a part of the conductor extended therethrough, tubular second means mounted on the first means for movement relative the first means between a first position to retain the above at least a part of the conductor in the chamber and a second position to permit movement thereof into and out of the chamber, clamp third means joined to one of the first and second means and operative between a head clamping position and a clamp head release position, and operating fourth means joined to the other of the first and second means for operating the clamp means from its clamping position to its release position when the second means is moved relative the first means from its first position to its second position.

27. The tool of claim 26 further characterized in that the first and fourth means have wall means defining a bore for receiving another part of the conductor, the first and fourth means being joined in fixed relationship to one another.

28. The apparatus of claim 26 further characterized in that the clamp means comprises an annular clamp segment mounting portion, and a plurality of axially elongated, circumferentially spaced clamp segments movable between a release position and a clamped position, said clamp segments having first ends joined to the clamp segment mounting portion and axially opposite terminal ends.

29. The tool of claim 28 further characterized in that the clamp means is made of resilient material whereby the clamp segments are resiliently retained in a clamped position.

30. The tool of claim 28 further characterized in that the fourth means comprises cam means for moving the clamp segments from their clamped position to their release position.

31. The tool of claim 26 further characterized in that the second means has means for rotatably mounting the first means and blocking any substantial relative axial movement.

32. The tool of claim 31 further characterized in that the clamp means has means defining a plurality of circumferentially spaced, cam operated clamp segments defining a bore portion having a central axis and operable between a clamping position and a release position, and that the fourth means comprises a cam extending into the clamp segments bore portion for operating the clamp segments from their clamped position to their release position.

33. The tool of claim 33 wherein the lead head has a notch and a head extension opposite the head notch, further characterized in that each of the clamp segments has a terminal end, that one of the clamp segments has adjacent its terminal end, an abutment extending radially inwardly toward the central axis that is adapted to move into the head notch and that clamp means has an axially outwardly opening notch generally diametrically opposite the abutment that is adapted to receive the head extension.

34. A body tissue lead installation tool for clampingly holding the electrode head of a lead for conducting electrical impulses to body tissue, comprising an axially elongated electrode holder assembly that includes a tubular clamp having a first end portion and a second end, said clamp having a plurality of axially elongated slots opening to the clamp second end to provide a plurality of clamp segments that are movable between a head clamping position and a head release position, and tubular means having a central axis, a first end joined to the clamp first end portion to mount the clamp and an axially remote second end,
    cam means rotatable in the tubular clamp for moving the clamp segments from their clamping position to their release position, and operator means movably mounted by the tubular means for rotating the cam means to move the clamp segments from their clamping position to their release position.

35. The apparatus of claim 34 further characterized in that the clamp is made of resilient material to resiliently retain the clamp segments in their clamping position.

36. The apparatus of claim 34 further characterized in that the tubular means and operator means have cooperating means for maintaining the cam means substantially axially spaced from clamp second end.

37. The apparatus of claim 34 further characterized in that the operator means includes an axially elongated member extended into the tubular means for rotation about said central axis and that the cam means has a cam surface for each clamp segment for moving a clamp segment to its release position, the cam surfaces being equally radially spaced from said central axis.

38. The apparatus of claim 37 further characterized in that the clamp is made of a resilient material to resiliently retain the clamp segments in their clamping position and that the operator means has a surface that abuts against the tubular means to retain the cam means substantially spaced from the clamp second end.

39. The apparatus of claim 37 further characterized in that the clamp has at least three clamp segments.

* * * * *